(12) United States Patent
Fuggle

(10) Patent No.: US 6,353,323 B1
(45) Date of Patent: *Mar. 5, 2002

(54) ION CONCENTRATION AND PH MEASUREMENT

(75) Inventor: Graham Anthony Fuggle, North Harrow (GB)

(73) Assignee: Eastman Kodak Company, Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/128,565

(22) Filed: Aug. 4, 1998

(30) Foreign Application Priority Data

Dec. 13, 1997 (GB) .............................................. 9726348

(51) Int. Cl.[7] ............................................. G01N 27/416
(52) U.S. Cl. ...................................... 324/438; 324/425
(58) Field of Search ................................ 324/438, 459, 324/425, 434, 444, 71.1; 204/406, 416

(56) References Cited

U.S. PATENT DOCUMENTS

| 3,862,895 A | | 1/1975 | King et al. ................... 204/406 |
| 4,506,226 A | * | 3/1985 | Luce et al. .................. 324/459 |
| 4,641,249 A | * | 2/1987 | Gion et al. .............. 324/438 X |
| 4,816,131 A | | 3/1989 | Bomsztyk .................... 204/403 |
| 5,250,168 A | * | 10/1993 | Tsukada et al. ............. 204/416 |
| 5,336,388 A | * | 8/1994 | Leader et al. ................ 204/306 |

FOREIGN PATENT DOCUMENTS

| EP | 0 390 692 A | 10/1990 |
| EP | 0 450 473 A | 10/1991 |

* cited by examiner

Primary Examiner—Safet Metjahic
Assistant Examiner—T. R. Sundaram
(74) Attorney, Agent, or Firm—Susan L. Parulski; Clyde E. Bailey, Sr.

(57) ABSTRACT

Apparatus for, and a method of, simultaneously measuring the concentration of a selected ion species in a solution and the pH of the solution, uses an ion selective electrode, a reference electrode and an ISFET immersed in the solution. The ion concentration is determined in a first circuit from the potential difference between the ion selective electrode and the reference electrode, and the pH is determined in a second circuit from the current flowing between the ISFET and the reference electrode. The reference electrode is connected into the second circuit via a high resistance so as to isolate the two circuits from each other. The earth potential of the solution is connected to provide the earth potential of the first circuit, and is connected to the second circuit via a high capacitance so as to provide a virtual earth thereforee. Each circuit is supplied from a separate power source, and the circuit outputs are supplied via respective isolation amplifiers to a multi-channel meter.

16 Claims, 1 Drawing Sheet

US 6,353,323 B1

ION CONCENTRATION AND PH MEASUREMENT

FIELD OF THE INVENTION

This invention relates to the simultaneous measurement of the concentration of a selected ion species in a solution and the pH of the solution. The invention particularly, though not exclusively, relates to photographic solutions, and particularly, though not exclusively, where the selected ion species is silver. In general, however, the invention relates to the simultaneous potentiometric measurement of the concentration of any ion species in a solution and measurement of the pH of the solution using an ISFET (Ion Selective Field Effect Transistor).

BACKGROUND OF THE INVENTION

For the present purpose the tern "solution" is to be understood as also including an emulsion, for example a mixture of a silver compound suspended in gelatin, or a dispersion. The invention will be particularly described, by way of example only, with reference to photographic solutions.

It is known simultaneously to measure silver ion concentration in, and the pH of, an aqueous solution. In one arrangement, a single reference electrode is connected into a first potentiometer circuit with a conventional glass pH electrode, and is connected into a second potentiometer circuit with a conventional silver electrode, all three electrodes being immersed in the solution. In another arrangement, an ISFET is used instead of the glass pH electrode. This necessitates the use of a separate reference electrode for each measuring circuit in order to provide electrical isolation between the circuits since the ISFET is a current carrying device whose presence would otherwise interfere with the voltage measurement of the silver electrode.

A glass pH electrode has the disadvantage that it can be damaged under conditions of high temperature and high pH, so that its readings become unreliable or inconsistent. An ISFET overcomes this disadvantage. However, the conventional arrangement including an ISFET described above is complicated by the requirement of the additional reference electrode, especially when applied in a large scale production vessel, as used in the preparation of photographic emulsions for example, where the electrodes are configured in a unitary probe. This can lead to difficulties for maintenance and for calibration. Furthermore, existing probe structures would require extensive modification to accommodate the additional reference electrode, which would be expensive.

It will be appreciated that if, on the other hand, measurement of ion concentration and pH were not required simultaneously, then the measurements would not interfere with each other and a single reference electrode could be used successively in combination with an ion concentration electrode and an ISFET.

SUMMARY OF THE INVENTION

In accordance with one aspect of the present invention, there is provided apparatus for simultaneously measuring the concentration of a selected ion species in a solution and the pH of the solution, comprising: a first electrical circuit that is arranged to receive signals from both a reference electrode and an ion selective electrode immersed in the solution and to derive therefrom an output signal representative of the concentration of the selected ion in the solution; a second electrical circuit that is arranged to receive signals from both said reference electrode and an ISFET immersed in the solution and to derive therefrom an output signal representative of the pH of the solution; wherein any d.c. input signal to said first electrical circuit from the reference electrode is substantially electrically isolated from the input of the second circuit; wherein a signal representative of the voltage, usually earth potential, of the solution is supplied (a) directly to the first circuit so as to establish a reference, usually earth, potential for the first circuit, and (b) to the second circuit through a.c. coupling means so as to establish a corresponding virtual reference, usually earth, potential for the second circuit; and wherein the first and second electrical circuits are arranged to be provided with electrical power from supplies that are electrically isolated from each other.

The apparatus may comprise means for displaying a representation of said ion concentration and pH output signals, wherein said second electrical circuit includes an isolation amplifier, and wherein said display means is arranged to receive said pH output signal of the second circuit through the isolation amplifier. Preferably, the apparatus includes a further isolation amplifier through which the ion concentration output signal of the first circuit is supplied to the display means. Advantageously, the apparatus comprises a low pass filter, wherein said pH output signal from the second electrical circuit is arranged to be passed to the display means through the low pass filter.

Preferably, the apparatus comprises a high value resistor, for example of about 1 MΩ or greater, that is arranged to effect said electrical isolation of d.c. input signals to said first and second electrical circuits. Also said a.c. coupling means may comprise a high value capacitor, for example of about 1 μF or greater.

In accordance with another aspect of the present invention, there is provided a method of simultaneously measuring the concentration of a selected ion species in a solution and the pH of the solution, comprising the steps of: measuring in a first electrical circuit the potential difference between an ion selective electrode and a reference electrode both immersed in the solution, and deriving therefrom the concentration of the ions in the solution; measuring in a second electrical circuit the current flowing between an ISFET and the reference electrode both immersed in the solution, and deriving therefrom the pH of the solution; connecting the reference electrode to the first and second electrical circuits such that any d.c. signal from the reference electrode is electrically isolated from the second circuit; making an electrical connection between the solution and the first circuit so as to provide the solution potential as a reference, preferably earth, potential therefore, and making an electrical connection between the solution and the second circuit through a.c. coupling means so as to provide a corresponding virtual reference, preferably earth, potential therefore; and supplying the first and second circuits with electrical power from sources that are electrically isolated from each other.

The method of the invention is advantageously carried out using the apparatus of the invention.

Details of electrodes suitable for use in the present invention as ion selective and reference electrodes, and of ISFETs, can be found in the book "pH Measurement" by Helmuth Galster (VCH,1991).

The electrical isolation of the two circuits provided in the present invention allows an ISFET to be used in the pH measuring circuit, whilst needing only a single, common, reference electrode. The disadvantages of the known arrangements for simultaneous ion concentration and pH measurement are thus overcome in a particularly convenient manner.

The isolation is provided at several stages. Initially this is done by arranging that the signal from the reference electrode is used in the ion concentration circuit as a potentiometric measurement, and is supplied to the pH measuring circuit only as an a.c. input, i.e. after having any d.c. component isolated therefrom. An actual reference potential, the potential, usually earth, of the solution, is applied to the first circuit, and a virtual reference potential derived therefrom is applied to the second circuit. The two circuits have separate isolated power supplies. Furthermore, when the resulting ion concentration and pH signals are supplied to a display means, such as a multi-channel voltmeter, this is done through respective isolation amplifiers, which are preferably supplied from a third, isolated power supply.

The ability to use a single reference electrode means that a single, unitary measurement probe can be constructed, in which the ISFET can be installed relatively easily along with the ion selective and reference electrodes. Furthermore, the measuring apparatus can be calibrated more easily than is the case with the known arrangement using two reference electrodes.

Although described with reference to a single ion selective electrode and a single ISFET, it is envisaged that the present invention may comprise two or more ion concentration electrodes and/or two or more ISFETs, each type of electrode being connected into the respective first or second electrical circuit.

BRIEF DESCRIPTION OF THE DRAWINGS

Apparatus for, and a method of, simultaneously measuring the concentration of a selected ion species in a solution and the pH of the solution, will now be described, by way of example, with reference to the accompanying schematic circuit diagram.

DETAILED DESCRIPTION OF THE INVENTION

Figure 1:
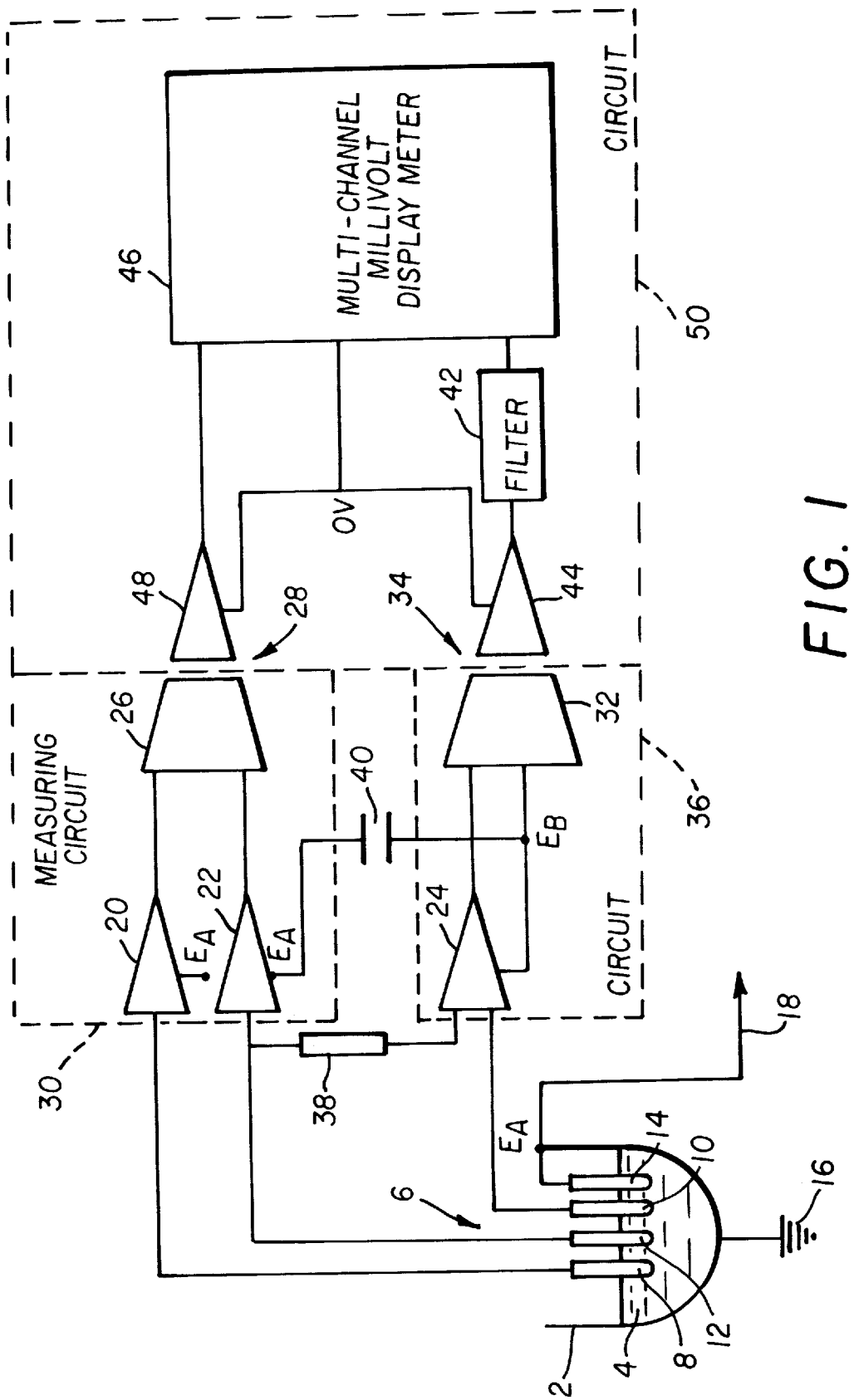

Referring to the drawing, a metal kettle 2 contains an aqueous solution of a photographic emulsion 4. It is desired simultaneously to monitor and/or to control the concentration of silver ions in the solution 4 and the pH of the solution 4. To this end, a unitary probe 6 is immersed in the solution 4. The probe 6 comprises a silver electrode 8, an ISFET 10, a reference electrode 12 and a ground electrode 14. The ground electrode 14 is connected to the kettle 2, which is earthed at 16, and provides an earth reference potential $E_A$ on line 18.

The silver electrode 8 and reference electrode 12 are connected to respective preamplifiers 20 and 22. Output signals from the amplifiers 20,22 are supplied to respective terminals of an input stage 26 of a first differential optical isolation amplifier 28. Line 18 is connected to each of the amplifiers 20,22 and 26 so as to provide the earthed signal reference voltage $E_A$ therefore. The silver ion concentration measuring circuit 30 comprising the amplifiers 20,22 and 26 is energised by an isolated ±15 V,0 V power supply (not shown).

The ISFET 10 is connected to a preamplifier 24 that converts the current signal from the ISFET 10 into a voltage signal, typically of the value of a few millivolts. The output signal from the amplifier 24 is supplied to a terminal of an input stage 32 of a second differential optical isolation amplifier 34. The pH measuring circuit 36 comprising the amplifiers 24 and 32 is energised by a separate, isolated ±15 V,0 V power supply (not shown).

The ISFET amplifier 24 requires a signal from the reference electrode 12, and this is derived from the silver measurement circuit via a 2 MΩ resistor 38. The resistor 38, and in particular its high value, provides d.c. isolation of the input to each of the measuring circuits from the common reference electrode 12.

For the ISFET amplifier 24 to operate correctly, the earth reference voltage $E_A$ of the circuit 30 must be linked to the 0 volt level of the circuit 36. However, to do this directly would also put the silver electrode 8 in the same circuit. In that case, the d.c. current drawn by the silver electrode 8 would be sufficient to corrupt the pH measurement of the circuit 36. Since the ISFET circuit 36 is subject to line frequency in its unreferenced state, a virtual earth is provided by connecting a high impedance capacitor 40 of 1 μF between the $E_A$ voltage on line 18 as supplied to the circuit 30 and the 0 volt level, $E_B$, of circuit 36, and at the same time the d.c. current from the silver electrode 8 is blocked. Using this technique, the ISFET measurement of the circuit 36 is modulated by the line frequency, and so a low pass (25 Hz) filter 42 is inserted between the output stage 44 of the second isolation amplifier 34 and a multi-channel millivolt display meter 46. Output stage 48 of the first isolation amplifier 28 is also supplied to the meter 46, together with a 0 volt reference signal from each of the output stages 44,48 of the isolation amplifiers 28,34 respectively.

Isolation of the ion concentration and pH measurements is completed by employing a third, isolated power supply (not shown) for the circuit 50, comprising the isolation amplifier output stages 44,48, filter 42 and meter 46.

Although a separate ground electrode 14 is shown, it will be appreciated that the potential of the solution 4 may alternatively be supplied to the measuring circuits 30,36 directly from the earthed kettle 2 itself.

Although amplifier 28 is shown as being an isolation amplifier, this is not essential for providing the electrical isolation that is required in the present invention.

Although it is necessary to isolate the power supplies to the separate measuring circuits 30,36, one or the other of these could also perform the function of the third power supply, for the circuit 50.

It is envisaged that the measuring circuits, such as electrical circuits 30,36 and 50, may be used in connection with two, or more, ion concentration electrodes and/or two, or more, ISFETs. In such an arrangement, the connections from the electrode(s) and ISFET(s) are to be made into additional respective amplifiers, such as the amplifiers 20 and 24, each having its own connection to a resistor, such as the resistor 38, and capacitor, such as capacitor 40, as appropriate, and to a solution reference potential, such as provided by line 18.

What is claimed is:

1. Apparatus for simultaneously measuring the concentration of a selected ion species in a solution and the pH of the solution, comprising:

a first electrical circuit that is arranged to receive signals from both a reference electrode and an ion selective electrode immersed in the solution and to derive therefrom an output signal representative of the concentration of the selected ion in the solution, a second electrical circuit that is arranged to receive signals from both said reference electrode and an ISFET immersed in the solution and to derive therefrom an output signal representative of the pH of the solution;

a.c. coupling means arranged between said first electrical circuit and said second electrical circuit; and means for electrically isolating said first electrical circuit and said second electrical circuit such that any d.c. input signal to said first electrical circuit from the reference electrode is substantially electrically isolated from the input of the second circuit;

wherein a signal representative of the voltage, usually earth potential, of the solution is supplied (a) directly to the first circuit so as to establish a reference, usually earth, potential for the first circuit, and (b) to the second circuit through said a.c coupling means so as to establish a corresponding virtual reference, usually earth, potential for the second circuit; and wherein the first and second electrical circuits are arranged to be provided with electrical power from supplies that are electrically isolated from each other.

2. Apparatus according to claim 1, comprising means for displaying a representation of said ion concentration and pH output signals, wherein said second electrical circuit includes an isolation amplifier, and wherein said display means is arranged to receive said pH output signal of the second circuit through the isolation amplifier.

3. Apparatus according to claim 2, including a further isolation amplifier through which the ion concentration output signal of the first circuit is supplied to the display means.

4. Apparatus according to claim 2, comprising a low pass filter, wherein said pH output signal from the second electrical circuit is arranged to be passed to the display means through the low pass filter.

5. Apparatus according to claim 1, wherein the first electrical circuit comprises two pre-amplifiers arranged to receive respective ones of the signals from the reference electrode and the ion selective electrode, and a subsequent differential amplifier stage for deriving the ion concentration output signal.

6. Apparatus according to claim 1, comprising a (high value) resistor that is arranged to effect said electrical isolation of d.c. input signals to said first and second electrical circuits.

7. Apparatus according to claim 1, wherein said a.c. coupling means comprises a (high value) capacitor.

8. Apparatus according to claim 1, comprising an ion selective electrode, an ISFET, and a reference electrode, for supplying said signals to the first and second electrical circuits.

9. Apparatus according to claim 1, comprising an electrode arranged to be exposed to the solution for producing said signal representative of the potential thereof.

10. Apparatus according to claim 9, wherein said solution potential electrode comprises an electrically conductive vessel for containing the solution.

11. Apparatus according to claim 2 wherein the isolation amplifier comprises an optical isolation amplifier.

12. Apparatus according to claim 1, comprising a first electrical power supply for supplying power to said first electrical circuit, and a second electrical power supply for supplying power to said second electrical circuit, said first and second power supplies being electrically isolated from each other.

13. A method of simultaneously measuring the concentration of a selected ion species in a solution and the pH of the solution, comprising the steps of:

measuring in a first electrical circuit the potential difference between an ion selective electrode and a reference electrode both immersed in the solution, and deriving therefrom the concentration of the ions in the solution;

measuring in a second electrical circuit the current flowing between an ISFET and the reference electrode both immersed in the solution, and deriving therefrom the pH of the solution;

connecting the reference electrode to the first and second electrical circuits such that any d.c. signal from the reference electrode is electrically isolated from the second circuit;

making an electrical connection between the solution and the first circuit so as to provide the solution potential as a reference, preferably earth, potential therefore, and making an electrical connection between the solution and the second circuit through a.c. coupling means so as to provide a corresponding virtual reference, preferably earth, potential therefore; and supplying the first and second circuits with electrical power from sources that are electrically isolated from each other.

14. A method according to claim 13, wherein the signals derived in the first and second circuits are supplied to display means through respective isolation amplifiers.

15. A method according to claim 14, wherein the signal from the second circuit is supplied to the display means through a low pass filter.

16. A method according to claim 14, wherein the isolation amplifiers are supplied with electrical power from a third source that is electrically isolated from the said sources.

* * * * *